(12) United States Patent
Meier et al.

(10) Patent No.: US 7,022,115 B1
(45) Date of Patent: Apr. 4, 2006

(54) CONTINUOUSLY CONDUCTIVE UNIPOLAR CANNULA FOR ANESTHESIA

(76) Inventors: Gisela Meier, Untere Greinbächl 21A, 82418 Murnau (DE); Heinrich Pajunk, Am Holzplatz 5-7, 78187 Geisingen (DE); Horst Pajunk, Am Holzplatz 5-7, 78187 Geisingen (DE)

( * ) Notice: Subject to any disclaimer, the term of this patent is extended or adjusted under 35 U.S.C. 154(b) by 0 days.

(21) Appl. No.: 09/438,759

(22) Filed: Nov. 11, 1999

(51) Int. Cl.
*A61M 31/00* (2006.01)

(52) U.S. Cl. .................. 604/500; 604/20; 604/164.11; 604/264

(58) Field of Classification Search .................. 604/20, 604/21, 22, 27, 264–272, 523, 164.01–165.02, 604/93.01, 500
See application file for complete search history.

(56) References Cited

U.S. PATENT DOCUMENTS

| | | | | |
|---|---|---|---|---|
| 4,765,341 A | * | 8/1988 | Mower et al. | 128/348 |
| 4,776,847 A | * | 10/1988 | Krebs | 604/164.06 |
| 4,842,585 A | * | 6/1989 | Witt | 604/158 |
| 4,889,529 A | * | 12/1989 | Haindl | 604/274 |
| 5,536,240 A | * | 7/1996 | Edwards et al. | 604/22 |
| 5,665,096 A | * | 9/1997 | Yoon | 606/139 |
| 5,720,718 A | * | 2/1998 | Rosen et al. | 604/22 |
| 5,730,742 A | * | 3/1998 | Wojciechowicz | 606/49 |
| 5,976,110 A | | 11/1999 | Greengrass et al. | |
| 6,286,512 B1 | * | 9/2001 | Loeb et al. | 128/898 |
| 6,306,132 B1 | * | 10/2001 | Moorman et al. | 606/41 |
| 6,337,994 B1 | * | 1/2002 | Stoianovici et al. | 600/547 |

FOREIGN PATENT DOCUMENTS

| | | |
|---|---|---|
| DE | 30 20 926 C2 | 11/1983 |
| DE | 44 20 232 A1 | 12/1995 |
| EP | 0 303 824 | 2/1989 |

* cited by examiner

*Primary Examiner*—Long V. Le
*Assistant Examiner*—Ann Y. Lam
(74) *Attorney, Agent, or Firm*—Akerman Senterfitt; Stephan A. Pendorf

(57) ABSTRACT

A continuously conductive unipolar cannula for anesthesia is described with an electrically conductive cannula tube (10), with a tip (14) at the distal end and a body part (18) at the proximal end. The cannula tube (10) is provided with an outer electrically insulating covering, which leaves exposed only an end area (16) of the distal tip (14). In the area of the body part (18), an electrically contacting connection (22, 24, 26) for electro-stimulation is provided, which is provided radially on the outer circumference of the cannula tube (10). The body part (18) includes a guide inlet opening (32, 34) axially aligned with the cannula tube (10), through which a catheter can be introduced in the cannula tube (10). Alternatively, an injection hose or a needle can be connected to the body part (18).

16 Claims, 2 Drawing Sheets

CONTINUOUSLY CONDUCTIVE UNIPOLAR CANNULA FOR ANESTHESIA

BACKGROUND OF THE INVENTION

1. Field of the Invention

The invention concerns a continuously conductive unipolar cannula for anesthesia.

2. Description of the Relate Art

A continuously conductive unipolar cannula for anesthesia produced by the company Pajunk GmbH, D-78187, Geisingen, Germany is known, which has an electrically conductive cannula tube, the tube having an electrically insulated outer covering which extends from the proximal body part out to the distal tip of the cannula tube and leaves exposed the distal tip in its distal end area. In the area of the proximal body part, the cannula tube is electrically contacted with a connector, which can be connected to an electro-stimulation device via a socket or jack. The distal tip of the cannula tube is either provided with a facet cut or is designed as a so-called Sprotte tip as disclosed in DE 30 20 926 C2.

In this known unipolar cannula, the connector for electro-stimulation and an injection hose for the anesthetic are provided introduced axially parallel next to each other in the proximal end face of the body part of the cannula tube. The unipolar cannula can be placed exactly in the nerve sheath with its distal tip using electro-stimulation, in order to then be able to apply the anesthetic via the feed hose precisely on the nerve.

In the continuously conductive anesthesia, a catheter is placed in the nerve sheath, in order to be able to introduce anesthetic over a longer period of time. In order to introduce a catheter using the known unipolar cannula, a plastic introducer cannula is pulled over the cannula tube, which is placed under electro-stimulation by means of the unipolar cannula. As soon as the plastic introducer cannula is in place, the unipolar cannula is withdrawn and then the catheter can be introduced through the plastic introduction cannula.

It is further known from DE 36 43 235 C1 and DE 37 12 869 C2, to design a cannula with Sprotte-tip, such that through this cannula itself a catheter can be introduced in place. For this, a ramp or guide is formed in the inside of the distal tip of the cannula tube, which leads to a side outlet opening. A catheter introduced proximally in the cannula tube is led out of the cannula tube via this ramp through the side outlet opening. This cannula is suitable for the placement of a catheter without a supplemental introducer cannula. An electro-stimulation is, however, not possible with this known cannula. Accordingly, this cannula is not provided with an electrical connection for electro-stimulation.

SUMMARY OF THE INVENTION

The invention is concerned with the task, of providing a unipolar cannula for the continuous conduction anesthesia, which through simple construction and simple operation unites the placement of the catheter with the advantage of the electro-stimulation.

This task is inventively solved by the unipolar cannula with the characteristics of claim 1.

The inventive unipolar cannula can be placed or located with the help of electrical nerve stimulation. The outer insulating covering of the cannula tube, which leaves only a very small, almost pinpoint area of the tip free, makes possible an extraordinarily precise placement of the tip. The unipolar cannula can itself be used for the guided introduction of the catheter, for which the body part positioned at the proximal end of the cannula tube exhibits an introduction opening, which leads axially aligned into the cannula tube. The connection for electro-stimulation is introduced through the side of the body part and contacts the outside of the electrically conductive cannula tube. The connection thus does not impede or constrict therewith the axial inlet opening of the body part. After the placement of the unipolar cannula with the help of electro-stimulation, the catheter can be introduced through the cannula tube, without any requirement that the position of the unipolar cannula must be changed or other measures be taken. Preferably, a releasable or removeable connection is formed with the body part at the introduction opening, preferably a luer-lock connection. At this connection, an injection hose can be connected if desired, for injection of an initial or a short duration anesthetic. Likewise, a needle can be connected to the releasable connection, for injection of an anesthetic or also for fluids for aspiration for position control. The possibility of using the body part both for the alternative connection of an injection hose or a needle as well as for introduction of the catheter makes the unipolar cannula extremely versatile. This versatility is achieved using an extremely simple and economical design. The manipulation of the unipolar cannula is likewise extremely simple, since the cannula can be employed without changing the position both for the injection or aspiration as well as for the introduction of the catheter. The axially aligned connection of a needle at the proximal body part makes possible also the carrying out of the nerve block with a one-hand technique.

The needle of the cannular tube can be designed with a facet cut, so that the outlet opening is formed by the diagonal cut surface slanted with respect to the cannula axis. In this embodiment, the catheter exits out of the distal needle axially aligned with the cannula tube. This design is suitable, for example, for the continuous blockage of the interior ischiadicus, for the positioning of a distal ischiadicus catheter, or for the seating of a psoas compartment block.

Likewise, the distal tip of the cannula tube can be designed as a Sprotte-tip wherein the catheter, which is introduced through the cannula tube, is guided through the side outlet openings behind the tip by means of a ramp. The catheter thereby exits at an angle of approximately 30° to the cannula axis. This is of advantage in the anesthetic technique, in which a penetration or piercing essentially parallel to the nerve is not possible. This design of the unipolar cannula is employed, for example, in the interscalenary plexus blockage, the vertical-infraclavical plexus blockage, the ischiadicus blockage, and the blockage of the nervus suprascapularis.

BRIEF DESCRIPTION OF THE DRAWINGS

In the following, the invention will be described in greater detail on the basis of the embodiments shown in the drawing. There is shown.

FIGS. 1 and 2 show a first embodiment of the unipolar cannula.

DETAILED DESCRIPTION OF THE INVENTION

Figure 1:
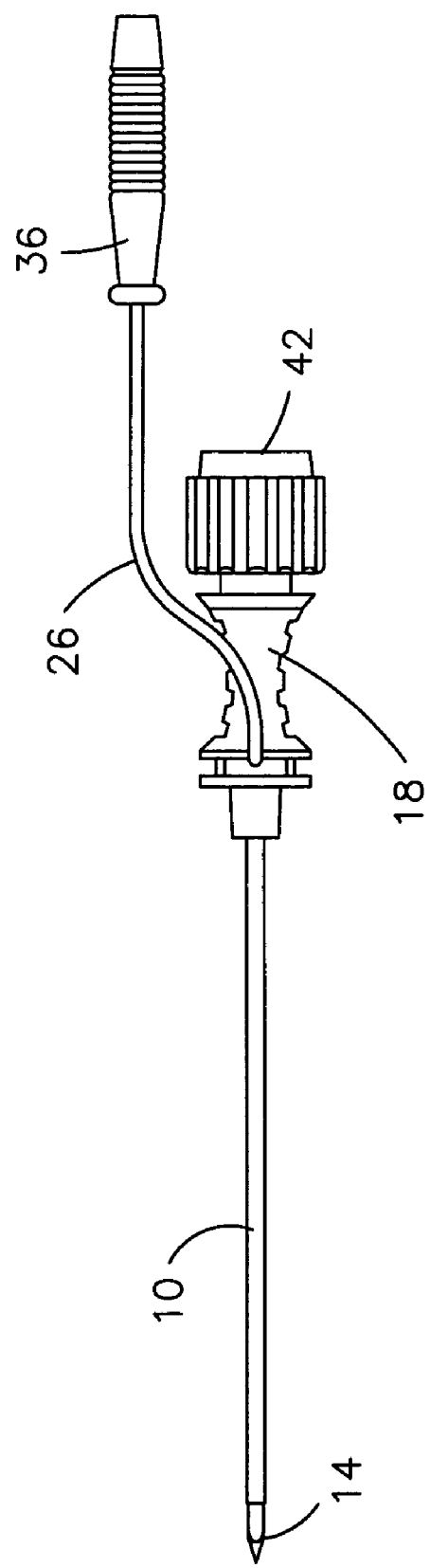
FIG. 1 a view of the unipolar cannula in a first embodiment.

This cannula includes an electrically conductive cannula tube 10, which is preferably formed of steel. Depending upon the model, the cannula tube 10 has a length of from 25 to 200 mm and a diameter of 0.5 to 11.0 mm. In the illustrative embodiment of FIGS. 1 and 2, the distal end of the cannula 10 is cut or ground Do with a facet cut 12 less than 45° to the axis of the cannula tube 10, so that a distal tip 14 is formed. The outer surface of the cannula tube 10 is covered with an electrically conductive plastic. The covering extends from the proximal end of the cannula tube 10 out to the distal tip 14 and leaves free only the distal end area 16 of the tip 14 with a length of maximally approximately 1 mm, in which the metal of the cannula tube 10 is exposed.

The proximal end of the cannula tube 10 is positioned co-axially in a body part 18 of plastic and is adhered therewith via a hardening adhesive 20. The body part 18 exhibits an essentially cylindrical shape through which a borehole extends co-axially.

In the distal area, the inner diameter of this borehole corresponds to the outer diameter of the cannula tube 10 seated in this borehole. The cannula tube 10 projects with its proximal end axially approximately into the middle of the body part 18. In the area of the proximal end of the cannula tube 10, the inner diameter of the body part 18 widens, so that between the inner wall of the body part 18 and the cannula tube 10 a ring gap remains free. In the area of this ring gap, a cylindrical connection socket or jack 22 in electrically conductive contact is pressed against the metallic cannula tube 10. A conductive wire 24 of a stranded conductor 26 is soldered this metallic connection junction 22. The non-insulated wire 24 runs in the area in which it is soldered with the connection junction 22 axially parallel to the cannula tube 10 in the distal direction. The insulated stranded conductor 26 then bends away at a right angle from this axially parallel direction and extends radially through the body part 18 towards the outside. The opening of the body part 18, through which the connection stranded conductor 26 exits, is filled with a hardening adhesive 28.

The ring gap between the inner wall of the bore of the body part 18 and the proximal end of the cannula tube 10 with the connection socket or jack 22 and the wire 24 is filled with a hardening plastic 30.

The plastic 30 forms an inlet funnel 32, which connects co-axially to the proximal end of the cannula tube 10 and widens from the inner diameter of the cannula tube 10 in proximal direction to the diameter of the internal bore of the body part 18. Connected with this introduction funnel 32 in the axially proximal direction is the section of the body part 18 designed as luer-lock connection 34, which axially aligns with the cannula tube 10.

On the free end of the stranded connector 26, a plug-in connector junction or jack 36 is provided, with which the unipolar cannula can be plugged into an electrical nerve stimulator. The nerve stimulator sends out electrical voltage impulses of a few milliamps, which are conducted to the exposed distal end area 16 of the tip 14 through the stranded conductor 26, the wire 24, the connector junction 22, and the cannula tube 10, in order to emits an electrical nerve stimulation for localization of the distal tip 14.

On the outer circumference of the body part 18, grip flanges 38 are provided. An indicator notch 40 in one of the grip flanges 38 makes it possible to recognize the angled position of the facet cut 12.

In order to place the unipolar cannula, this is connected by means of the plug-in connector 36 to a nerve stimulator. The cannula tube 10 is stuck into the nerve sheath via the cut tip 14, whereby the respective position of the tip 14 can be controlled via the electro-stimulation. If the distal tip 14 of the cannula tube 10 is in place, then an injection hose can be connected to the Luer-lock connection 34 by means of a Luer-lock connector 42, in order to introduce an anesthetic via the cannula tube 10. Alternatively, a needle can be connected to the Luer-lock connection 34 in order to control the position of the distal tip 14 by aspiration or in order to inject an anesthetic through this tip. If a catheter is to be placed for a long tern anesthesia, so this is—in certain cases after disconnection of the injection hose or the needle— axially introduced through the Luer-lock connection 34, whereby the inlet funnel 32 of the catheter tip leads into the cannula tube 10. The catheter tip passes axially out through the open distal end of the cannula tube 10 and is brought into the desired position. If the catheter is in place, so the unipolar cannula can be pulled out from the catheter from the back, whereby the catheter remains in its position.

Figure 3:
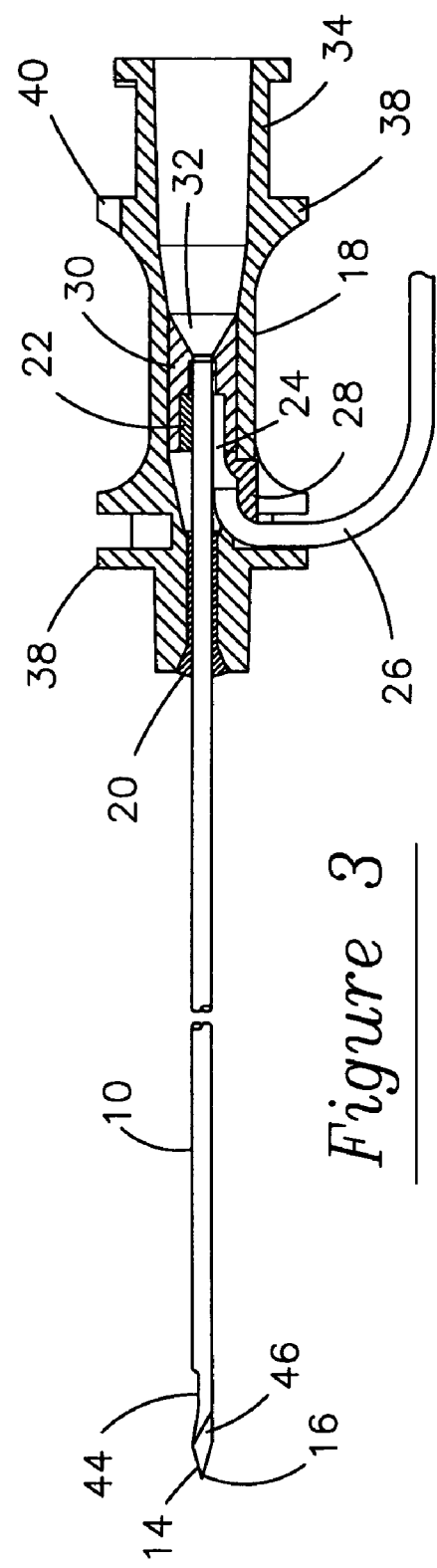
FIG. 3 an axial section corresponding to FIG. 2 of a second embodiment of the unipolar cannula.

FIG. 3 shows a further embodiment of the unipolar cannula. As far as this corresponds with the previously described embodiment, the same reference numbers are employed and reference is made to the above description.

Figure 2:
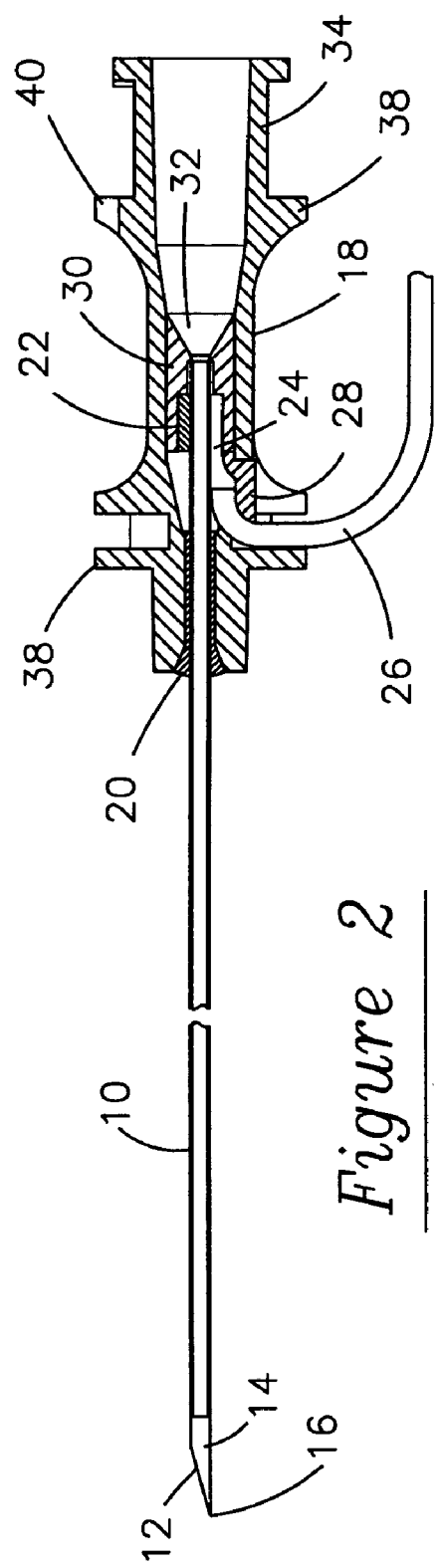
FIG. 2 an enlarged vertical section of this unipolar cannula.

In contrast to the embodiments of FIGS. 1 and 2, the distal tip 14 of the unipolar cannula of FIG. 3 is designed as a Sprotte-tip, as this is described in DE 36 43 235 C1. The distal tip 14 is designed as a closed-arched conical needle. Along the side behind the conical opening there is an outlet opening 44. The tip 14 is filled with a hardenable plastic 46, so that a ramp is formed on the inside of the cannula tube 10, which deflects the catheter tip out of the axial direction as it is slid distally towards the front in the cannula tube 10, so that the catheter exits from the side of the outlet opening 44 at an angle of approximately 30° to the axis of the cannula tube 10. The cannula tube 10 is covered with insulation up to the conically-arched tip 14 so that also here only a distal end area 16 of the tip 14 with a maximal length of 1 mm is exposed.

REFERENCE NUMBER LIST

10 Cannula tube
12 Facet cut
14 Distal tip
16 End area
18 Body part
20 Adhesive
22 Junction Box
24 Wire
26 Multi-stranded conductor
28 Adhesive
30 Plastic
32 Inlet funnel
34 Luer-lock connection
36 Plug-in connector
38 Grip flange
40 Marking groove
42 Luer-lock connector
44 Outlet opening
46 Plastic ramp

What is claimed is:

1. A cannula assembly for anesthesia comprising:
   a flexible catheter inside;
   an electrically conductive rigid hollow tube (10) the hollow tube formed by a steel tube including a proximal end and a distal end, the distal end including a sharp tip (14) and an exit opening in the area of the sharp tip (14) dimensioned for passage of the catheter, a body part (18) provided at the proximal end of the hollow tube (10), the body part (18) including an inlet opening (32, 34) axially aligned with the hollow tube (10) adapted for guiding the catheter for introduction into the proximal end of the hollow tube (10), and a connector (22, 24, 26) electrically connected to the hollow tube (10) in the area of the cannula body part (18) for transmission of electro-stimulation, wherein said hollow tube (10) has an electrically insulated outer covering extending from the body part (18) out to the sharp tip (14) and which leaves the sharp tip (14) exposed at least in its distal end area (16), and wherein said electrical connector (24, 26) extends through the body part (18) to the outer surface of the hollow tube (10) wherein the cannula is assembly unipolar.

2. A cannula assembly according to claim 1, wherein an electrical connection is formed between the electrical connector and hollow tube by an electrical contact pressed against the circumference of the hollow tube (10), to which a contact a wire (24) of a multi-strand connector (26) is soldered.

3. A cannula assembly according to claim 2, wherein the wire (24) lies axially parallel against the hollow tube (10), and the multi-strand conductor (26) runs radially through the body part (18) towards the outside.

4. A cannula assembly according to claim 1, wherein the proximal end of the hollow tube (10) is provided co-axially in the body part (18), wherein a ring gap is formed between (a) the proximal end of the hollow tube (10) and the thereto connected electrically contacting connector (22, 24) and (b) an inner wall of the body part (18), and wherein said ring gap is filled with plastic (30).

5. A cannula assembly according to claim 1, wherein the inlet opening of the body part (18) decreases in diameter to form an inlet funnel oriented co-axially towards the proximal end of the hollow tube (10).

6. A cannula assembly according to claim 1, wherein the proximal end of the body part (18) is a Luer-lock connection (34).

7. A cannula assembly according to claim 1, wherein the electrically exposed end area (16) of the distal tip (14) of the hollow tube (10) has a length of maximally 1 mm.

8. A cannula according to claim 1, wherein the distal tip (14) of the hollow tube (10) is formed as a closed conically arched tip with an exit opening (44) provided along a side of the hollow tube proximally behind this tip.

9. A cannula assembly according to claim 8, wherein a ramp (46) is formed on the inside of the distal end of the hollow tube (10), adapted to guide a catheter toward the exit opening on the side of the cannula.

10. A cannula assembly for anesthesia comprising:

a flexible catheter inside an electrically conductive rigid hollow tube (10) the hollow tube formed by a steel tube including a proximal end and a distal end, the distal end including a tip (14) and an exit opening in the area of the tip (14) dimensioned for passage of the catheter, a body part (18) provided at the proximal end of the hollow tube (10), the body part (18) including an inlet opening (32, 34) axially aligned with the hollow tube (10) adapted for guiding the catheter for introduction into the proximal end of the hollow tube (10), and a connector (22, 24, 26) electrically connected to the hollow tube (10) in the area of the cannula body part (18) for transmission of electro-stimulation, wherein said hollow tube (10) has an electrically insulated outer covering extending from the body part (18) out to the sharp tip (14) and which leaves the sharp tip (14) exposed at least in its distal end area (16), and wherein said electrical connector (24, 26) extends through the body part (18) to the outer surface of the hollow tube (10);

wherein the distal tip (14) of the cannula tube (10) is a facet cut (12)

and wherein the cannula assembly is unipolar.

11. A cannula assembly according to claim 10, wherein the facet cut (12) is angled at an angle of approximately 45° to a longitudinal axis of the hollow tube (10).

12. A cannula assembly for anesthesia comprising:

a flexible catheter inside a steel electrically conductive hollow tube (10) the hollow tube including a proximal end and a distal end, the distal end including a sharp tip (14) and an exit opening (12, 44) in the area of the tip (14) dimensioned for passage of the catheter, a body part (18) provided at the proximal end of the hollow tube (10), the body part (18) including an inlet opening (32, 34) axially aligned with the hollow tube (10) for guiding a catheter for introduction into the proximal end of the hollow tube (10), and a connector (22, 24, 26) electrically connected to the hollow tube (10) in the area of the cannula body part (18) for transmission of electro-stimulation, wherein said hollow tube (10) has an electrically insulated outer covering extending from the body part (18) out to the tip (14) and which leaves about 1 mm of the tip (14) exposed at least in its distal end area (16), and wherein said electrical connector (24, 26) extends through the body part (18) to the outer surface of the hollow tube (10)

wherein the cannula assembly is unipolar.

13. A cannula assembly as in claim 12, wherein said hollow tube tip is a Sprotte tip.

14. A cannula assembly as in claim 12, wherein said hollow tube tip is a facet cut tip.

15. A cannula assembly for anesthesia consisting of:

a flexible catheter inside an electrically conductive rigid hollow tube (10) the hollow tube formed by a steel tube including a proximal end and a distal end, the distal end including a sharp tip (14) and an exit opening in the area of the sharp tip (14) dimensioned for passage of the catheter, a body part (18) provided at the proximal end of the hollow tube (10), the body part (18) including an inlet opening (32, 34) axially aligned with the hollow tube (10) adapted for guiding the catheter for introduction into the proximal end of the hollow tube (10), and a connector (22, 24, 26) electrically connected to the hollow tube (10) in the area of the cannula body part (18) for transmission of electro-stimulation, wherein said hollow tube (10) has an electrically insulated outer covering extending from the body part (18) out to the sharp tip (14) and which leaves the sharp tip (14) exposed at least in its distal end area (16), and wherein said electrical connector (24, 26) extends through the body part (18) to the outer surface of the hollow tube (10) wherein the cannula assembly is unipolar.

16. A cannula assembly for anesthesia comprising:

a catheter inside an electrically conductive rigid hollow tube (10) the hollow tube formed by a steel tube including a proximal end and a distal end, the distal end including a sharp tip (14) and an exit opening in the area of the sharp tip (14) dimensioned for passage of the catheter, a body part (18) provided at the proximal end of the hollow tube (10), the body part (18) including a funnel shaped inlet opening (32, 34) axially aligned with the hollow tube (10) to insert the catheter into the proximal end of the hollow tube (10), and a connector (22, 24, 26) for transmission of electro-stimulation, wherein the connector passes through the body part and makes electrical contact with the hollow tube (10) in the area of the body part (18), wherein said hollow tube (10) has an electrically insulated outer covering extending from the body part (18) out to the sharp tip (14) and which leaves the sharp tip (14) exposed at least in its distal end area (16), and wherein said electrical connector (24, 26) extends through the body part (18) to the outer surface of the hollow tube (10) wherein the cannula is unipolar.

* * * * *